(12) United States Patent
Yang

(10) Patent No.: US 8,942,451 B2
(45) Date of Patent: Jan. 27, 2015

(54) METHOD AND SYSTEM FOR MAPPING TISSUE STATUS OF ACUTE STROKE

(75) Inventor: Qing Yang, Melbourne (AU)

(73) Assignee: Apollo Medical Imaging Technology Pty Ltd, Melbourne (AU)

( * ) Notice: Subject to any disclaimer, the term of this patent is extended or adjusted under 35 U.S.C. 154(b) by 428 days.

(21) Appl. No.: 13/128,645

(22) PCT Filed: Nov. 13, 2009

(86) PCT No.: PCT/IB2009/007446
§ 371 (c)(1),
(2), (4) Date: May 11, 2011

(87) PCT Pub. No.: WO2010/055405
PCT Pub. Date: May 20, 2010

(65) Prior Publication Data
US 2011/0229003 A1 Sep. 22, 2011

(30) Foreign Application Priority Data
Nov. 14, 2008 (AU) ............................ 2008905915

(51) Int. Cl.
*G06K 9/00* (2006.01)
*A61B 5/055* (2006.01)
*A61B 5/00* (2006.01)
*A61B 6/00* (2006.01)

(52) U.S. Cl.
CPC .............. *A61B 5/055* (2013.01); *A61B 5/416* (2013.01); *A61B 6/5217* (2013.01); *A61B 6/5247* (2013.01); *A61B 6/507* (2013.01); *A61B 6/501* (2013.01)

USPC .......................... 382/131; 382/128; 382/132

(58) Field of Classification Search
USPC ................................................ 382/128–132
See application file for complete search history.

(56) References Cited

U.S. PATENT DOCUMENTS 5,287,273 A * 2/1994 Kupfer et al. ................. 600/431
5,377,681 A * 1/1995 Drane ........................... 600/419
5,590,654 A * 1/1997 Prince .......................... 600/420

(Continued)

OTHER PUBLICATIONS

Leif Ostergaard, *David A. Chesler—Modeling Cerebral Blood Flow and Flow Heterogeneity From Magnetic Resonance Residue Data—Journal of Cerebral Blood Flow and Metabolism 19:690-699 © 1999.*

(Continued)

*Primary Examiner* — Chan Park
*Assistant Examiner* — Iman K Kholdebarin

(57) ABSTRACT

The current invention provides a method of identifying a ischemic lesion. The method includes loading perfusion imaging data into an electronic memory element and deriving perfusion maps from the perfusion imaging data, where the perfusion maps include a cerebral blood volume (CBV) map and an arterial delay time (DT) map, which utilize arterial delay and dispersion effects. Ischemic pixels are determined from the perfusion imaging data, where the DT is greater than a predetermined first threshold value and the CBV is below a second threshold value and the infarct portion of the ischemic lesion is determined, where DT is greater than a predetermined third threshold value and/or the CBV is below a forth threshold value. A cluster analysis is applied to all of the determined ischemic lesion and infarct pixels and the penumbra is then determined, where mismatch regions between the ischemic lesion and the infarct core define the penumbra.

17 Claims, 10 Drawing Sheets

(56) References Cited

U.S. PATENT DOCUMENTS

| | | | |
|---|---|---|---|
| 5,783,606 A * | 7/1998 | Tatton | 514/649 |
| 5,799,649 A * | 9/1998 | Prince | 600/420 |
| 5,853,370 A * | 12/1998 | Chance et al. | 600/473 |
| 5,924,987 A * | 7/1999 | Meaney et al. | 600/420 |
| 5,928,148 A * | 7/1999 | Wang et al. | 600/420 |
| 6,230,041 B1 * | 5/2001 | Prince | 600/420 |
| 6,397,097 B1 * | 5/2002 | Requardt | 600/431 |
| 6,760,611 B1 * | 7/2004 | Watanabe | 600/410 |
| 6,792,302 B2 * | 9/2004 | Wintermark et al. | 600/407 |
| 6,898,453 B2 * | 5/2005 | Lee | 600/407 |
| 7,069,068 B1 * | 6/2006 | Ostergaard | 600/420 |
| 7,308,124 B2 * | 12/2007 | Papageorgiou et al. | 382/128 |
| 7,512,435 B2 * | 3/2009 | Wu et al. | 600/431 |
| 7,539,528 B2 * | 5/2009 | Xiong et al. | 600/411 |
| 7,545,141 B2 * | 6/2009 | Kimura | 324/306 |
| 7,567,832 B2 * | 7/2009 | Schmainda et al. | 600/410 |
| 7,580,737 B2 * | 8/2009 | Wintermark et al. | 600/407 |
| 7,663,369 B2 * | 2/2010 | Kassai | 324/318 |
| 7,756,562 B2 * | 7/2010 | Kimura | 600/407 |
| 7,774,041 B2 * | 8/2010 | Nambu et al. | 600/407 |
| 7,826,885 B2 * | 11/2010 | Nambu et al. | 600/407 |
| 7,859,261 B2 * | 12/2010 | Jattke et al. | 324/307 |
| 7,933,468 B2 * | 4/2011 | Yang | 382/274 |
| 7,983,460 B2 * | 7/2011 | Licato et al. | 382/128 |
| 8,047,993 B2 * | 11/2011 | Shau et al. | 600/453 |
| 8,078,258 B2 * | 12/2011 | Declerck et al. | 600/420 |
| 8,115,482 B2 * | 2/2012 | Hughes | 324/309 |
| 8,125,484 B2 * | 2/2012 | Gering | 345/440 |
| 8,208,987 B2 * | 6/2012 | Hengerer et al. | 600/411 |
| 8,285,490 B2 * | 10/2012 | Yang | 702/19 |
| 8,417,317 B2 * | 4/2013 | Kabasawa | 600/420 |
| 8,427,151 B2 * | 4/2013 | Kao et al. | 324/307 |
| 2002/0177957 A1 * | 11/2002 | Lee | 702/19 |
| 2004/0096395 A1 * | 5/2004 | Xiong et al. | 424/9.1 |
| 2004/0138549 A1 * | 7/2004 | Wintermark et al. | 600/407 |
| 2006/0083687 A1 * | 4/2006 | Yang | 424/9.3 |
| 2006/0201504 A1 * | 9/2006 | Singhal et al. | 128/204.18 |
| 2008/0021502 A1 * | 1/2008 | Imielinska et al. | 607/1 |
| 2008/0208068 A1 * | 8/2008 | Robertson et al. | 600/508 |
| 2008/0300484 A1 * | 12/2008 | Wang et al. | 600/431 |
| 2009/0318794 A1 * | 12/2009 | DeCharms | 600/410 |
| 2011/0229003 A1 * | 9/2011 | Yang | 382/131 |

OTHER PUBLICATIONS

Christine C. Lee, Real-Time Adaptive Motion Correction in Functional MRI, From the Magnetic Resonance Research Laboratory, Mayo Clinic, Rochester, Minnesota, 1996.*

Leif Ostergaard, *David A. Chesler—Modeling Cerebral Blood Flow and Flow Heterogeneity From Magnetic Resonance Residue Data—Journal of Cerebral Blood Flow and Metabolism 19:690-699 © 1999.*

M. Heisen1, J. Buurman2—Impact of the arterial input function on the classification of contrast-agent uptake curves in dynamic contrast-enhanced (DCE) MR images based on heuristic shape modeling.*

Wolfgang Reith, Michael Forsting—Early MR Detection of Experimentally Induced Cerebral Ischemia Using Magnetic Susceptibility Contrast Agents: Comparison between Gadopentetate Dimeglumine and Iron Oxide Particles, AJNR Am J Neuroradiol 16:53-60, Jan. 1995.*

Reith et al., (Early MR Detection of Experimentally Induced Cerebral Ischemia Using Magnetic Susceptibility Contrast Agents: Comparsion between Gadopentetate Dimeglumine and Iron Oxide Particle, AJNR Am J Neuroradiol 16:53-60, Jan. 1995).*

* cited by examiner

METHOD AND SYSTEM FOR MAPPING TISSUE STATUS OF ACUTE STROKE

FIELD OF THE INVENTION

This invention relates to a method and system of identifying the ischemic lesion, particularly for identifying the penumbra and infarct regions reflecting the tissue status of acute stroke.

BACKGROUND

Stroke is one of the major diseases causing death and disability. While stroke can be hemorrhagic and ischemic, the majority of stroke is ischemic due to a sudden blockage of blood supply to whole or part of the brain. During a stroke, the viability of the ischemic lesion depends on the level and duration of compromised blood flow. Within hours of the onset of a stroke, the ischemic lesion can consist any of the two types of tissues: (1) an infarct core of irreversibly damaged tissue; and (2) a penumbra region with reduced blood flow that is at risk of further infarction, but the tissue is salvageable by quick restoration of blood supply to the region. The process of measuring blood perfusion hence identifying the infarct core and penumbra in acute stroke non-invasively can provide important information to a physician in order to determine an appropriate treatment regime for the patient, such as thrombolytic therapy for an acute ischemic stroke patient.

A number of systems pertaining to depicting the ischemic penumbra and infarct core in acute stroke have been disclosed. In general, the systems involve a contrast agent delivered as an intravascular bolus during a dynamic imaging session such as computerized tomography (CT) or magnetic resonance imaging (MRI). The temporal profile of the image intensity in a pixel or region of interest (ROI) reflects the characteristics of the contrast agent hence the blood passing through the vasculature. The typical method of obtaining quantitative perfusion indices involves several steps including: (a) convert the signal intensity profile to the contrast concentration profile depending on the type of imaging modality; (b) measure the arterial input function (AIF) from a feeding vessel to the tissue of interest; (c) extract the tissue impulse residue function (IRF) from the tissue profile and the AIF using deconvolution; (d) calculate quantitative perfusion indices including cerebral blood flow (CBF), cerebral blood volume (CBV) and mean transit time (MTT) using the IRF. It practice, it is difficult to measure the AIF from a blood vessel immediately feeding the tissue of interests. Instead, a global $AIF_g$ is often detected from a large blood vessel such as the internal carotid artery (ICA), middle cerebral artery (MCA), or anterior cerebral artery (ACA).

U.S. Pat. No. 6,792,302 describes a method using dynamic CT perfusion for creating penumbra and infarct images. Certain threshold values are applied to the measured cerebral blood flow (CBF) or mean transit time (MTT) to identify the ischemic lesion, which is further classified into lesion into penumbra and infarct by applying certain threshold values to the measured cerebral blood volume (CBV). However, the CBF and CBV values in normal gray matter are higher (usually about 2 to 3 times) than those in normal white matter, applying the same CBV or CBF threshold values to gray matter and white matter may not be able to delineate the penumbra and infarct regions accurately. Further, in the case of major vessel disease such as acute stroke, a measured global $AIF_g$ from a large artery is often associated with a delay and dispersion effect before it reaches the ischemic tissue, causing overestimation of the MTT and underestimation of the CBF calculated by the normal deconvolution technique. Hence method using MTT or CBF thresholds for identifying the ischemic lesion has the potential to systematically overestimate the extent of the ischemic lesion and the penumbra.

Another method for evaluating novel stroke treatments using a tissue risk map has been disclosed in International Patent Application (No. PCT/US01/03502), where a GLM algorithm is used combining $T_2$-weighted MRI, DWI, ADC (apparent diffusion coefficient), CBV, CBF and/or MTT measured by diffusion-weighted MRI (DWI) and perfusion-weighted MRI (PWI). Again there is no taking into the account the delay and dispersion effect, hence potential CBF underestimation and MTT overestimation may leads to overestimation of the ischemic lesion and penumbra.

U.S. Pat. No. 5,685,305 describes a MRI method for detection of abnormal blood flow by measuring the "arrival delay map" calculated from the signal intensity curve. Without using de-convolution of an AIF, the "arrival delay map" value can be influenced by the contrast injection rate and patient cardiac output for a specific scan. Hence this parameter is a relative indicator for the region with abnormal blood flow. Further, no dispersion effect has been taken into account, and there is no disclosure about how to identify the ischemic penumbra.

The International Patent Application No PCT/AU2004/000821 (to the present applicant) has disclosed a method for improved perfusion measurements by taking into account the delay and dispersion effect, resulting in more accurate perfusion measurements including CBF, CBV, MTT and DT (arterial delay time). However, there is no disclosure about how to identify the ischemic penumbra.

In addition, perfusion imaging data often has substantial noise fluctuations particularly for dynamic CT perfusion data acquired with protocols of low radiation dosage. The simple threshold method mentioned above may produce false candidate pixels as ischemic penumbra and infarct regions due to image noise. Therefore it is desirable to further apply cluster analysis to discriminate isolated small regions or pixels from larger clusters of connected pixels reflecting the true ischemic lesion.

The present invention seeks to substantially overcome, or at least ameliorate, any one or more of the abovementioned disadvantages.

SUMMARY OF THE INVENTION

According to a first aspect of the invention there is provided a method of identifying the ischemic lesion by:

(a) loading a perfusion imaging data into an electronic memory means;

(b) deriving perfusion maps including CBV and DT maps by taking into account arterial delay and dispersion effects; and (c) detecting ischemic pixels where DT is greater than a predetermined first threshold value and CBV is below a second threshold value;

(d) detecting the infarct portion of the ischemic lesion, where DT is greater than a predetermined third threshold value and/or CBV is below a forth threshold value;

(e) applying cluster analysis to all the detected ischemic lesion pixels and infarct pixels respectively by removing small islands or filling small holes with maximum cluster size below a predetermined fifth threshold value.

(f) identifying the penumbra as the mismatch regions between the ischemic lesion and the infarct core.

The method may further include the step of applying motion correction after loading the data to compensate for motion artefacts due to the movement over time of the subject, such as a tissue or organ. The method may further comprise the step of determining a global arterial input function ($AIF_g$) from a major artery, and a venous output function (VOF) from a large draining vein. The VOF can be used to scale up the $AIF_g$ profile to minimize a partial voluming effect from the $AIF_g$.

The method may further comprise the step for deriving various perfusion maps using a model-free deconvolution technique such as the singular value decomposition (SVD) technique, which can be modified by taking into account arterial delay and dispersion effects. Deconvolution of the $AIF_g$ from a tissue profile produces a tissue IRF, where the maximum of the IRF appears at certain time point, Tmax, where Tmax=0 reflects normal blood supply in normal tissue. However, Tmax>0 is often associated with acute ischemic lesion due to arterial delay and dispersion effect. Such arterial delay and dispersion effects can be taken into account by an arterial transport function base on International Patent Application No PCT/AU2004/000821, where the dispersion scan be determined by a relative dispersion factor and the delay time. The current invention further uses an iterative deconvolution approach by looping through a series of delay time values, $DT_i$, ranging from 0 to Tmax. For each delay time, a modelled arterial transport function is convolved with the measured global $AIF_g$ to produce an $AIF_i$, which is used for SVD deconvolution of the tissue curve to generate an $IRF_i$ with its maximum appears at Tmax(i). The actual delay time, DT, is determined as the minimum $DT_i$ value which produces Tmax(i)=0. Subsequently, CBF and CBV can be determined by the maximum and integral of $IFR_i$ respectively, with MTT=CBV/CBF.

The method may further comprise the step of repeating the iteration process on a pixel-by-pixel basis to produce various perfusion maps for further analysis in order to identify the ischemic lesion and penumbra.

The method further comprises setting the predetermined first value for DT threshold to be 3 or 4 sec.

The method further comprises setting the second value for CBV threshold to be 9 ml/100 g representing the low CBV limit for a blood vessel.

The method may further comprise setting the predetermined third value for DT threshold to be 10 sec.

The method may further comprises setting the forth value for CBV threshold to be 1.5 ml/100 g, or 50% of the average CBV value in normal tissue measured from the same subject.

The method may comprise the step of cluster analysis by applying morphological operators such as opening and closing with a kernel size determined by the predetermined fifth threshold value of minimum lesion size with a typical value of 3 to 5 mm.

According to a second aspect of the invention there is provided a computer program means to perform the steps (a) through to (f) according to the first aspect.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

Figure 1:
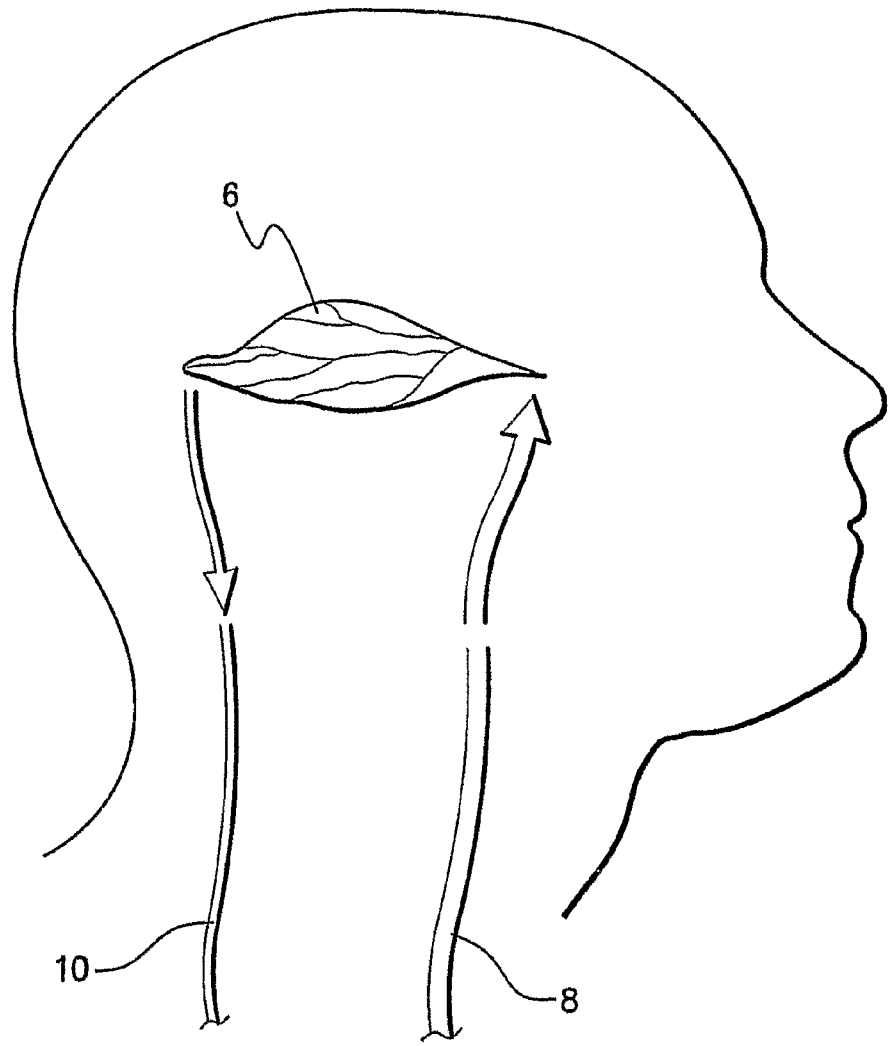
FIG. 1 is a side view of the head of the subject indicating flow of the contrast agent through a region of interest, such as a tissue.
Figure 2:
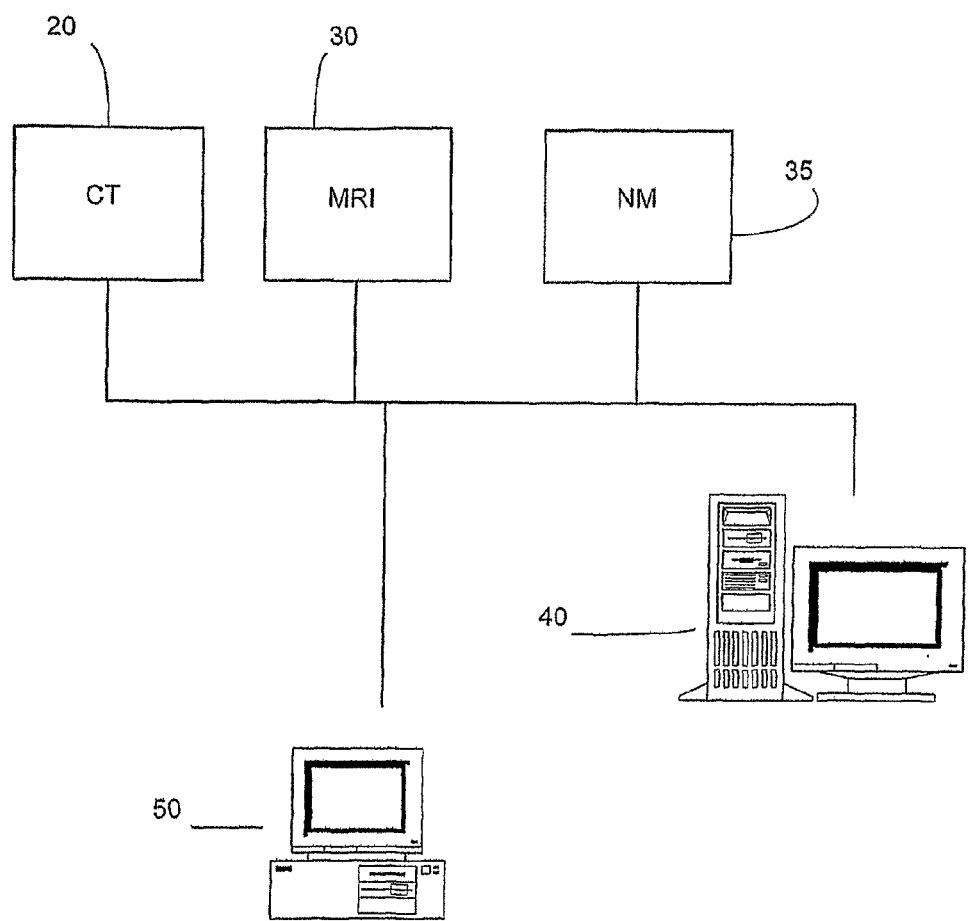
FIG. 2 is a block diagram showing a communications network including a number of scanners linked to a data storage system and a processing system.

The present invention is particularly applicable to CT, MRI and MN imaging systems. A bolus of contrasting agents is introduced via a needle into a patient at, for example, the arm of the patient. However the bolus can be input to any other part of the patient. A region of interest (ROI) may be a tissue 6 in a part of the patient's brain as shown in FIG. 1. Alternatively, the ROI may be a pixel or a plurality of pixels, where many pixels represent a calculated image to produce one or more perfusion maps. Blood circulating throughout the patient will contain the contrast agent and in particular may be delivered to the tissue 6 via artery 8 and the blood flowing through the tissue 6 is returned to the heart via vein 10. Raw data and/or images collected by a scan, such as from a CT scanner 20, MRI scanner 30 or NM scanner 35 are forwarded to a data storage system 40 in the form of a Picture Archiving Communications System (PACS) in FIG. 2. A computer program operating on a processor 50, in the form of a computer, is used to retrieve the various images or raw data from any one of the scanners 20, 30 or 35 or from the data storage system 40. The program then processes those images to provide an improved data set for a clinician to use, particularly in relation to perfusion indices including blood flow, blood volume, mean transit time, arterial delay time, arterial dispersion time or relative arterial dispersion, tissue dispersion time or relative tissue dispersion. The computer program need not reside on computer 50, but may reside in a console computer linked to any one of the scanners 20, 30 or 35. Alternatively the program may reside in a workstation (stand-alone or in a system) or in the PACS 40.

In order to select an appropriate arterial input function, AIF, various images (slices) from a scan are analysed to identify a major artery of interest. In CT the signal changes are directly proportional to the contrast agent concentration profile. However in MRI a mathematical conversion is used in order to convert the measured signal time-curve into contrast agent concentration profile. From the raw data retrieved, the program stored in the memory of system 50 automatically calculates the contrast concentration based on the measured signal intensities of the contrast agent. It then searches all pixels to find the optimal AIF (or VIF) based on the criteria of early arrival, high and narrow peak for AIF, and later arrival, high and broad peak with maximum peak area for VIF. The program displays the searched AIF and VIF pixels on the corresponding images and plots the AIF and VIF time-curves. A user may further select a particular pixel while dynamically viewing its profile against the selected AIF in order to confirm the best arterial input function. A better arterial pixel can be saved to replace or average with the saved AIF and then the user may "click" on further pixels in order to compare the further pixels with the updated AIF until the user is satisfied with the selected AIF. The selection of the best AIF may be done through different slices with the effort to minimize partial voluming (PV) where only a part of the artery is contained in the pixel. Similarly, the best VIP profile can be confirmed by the user.

Figure 5:
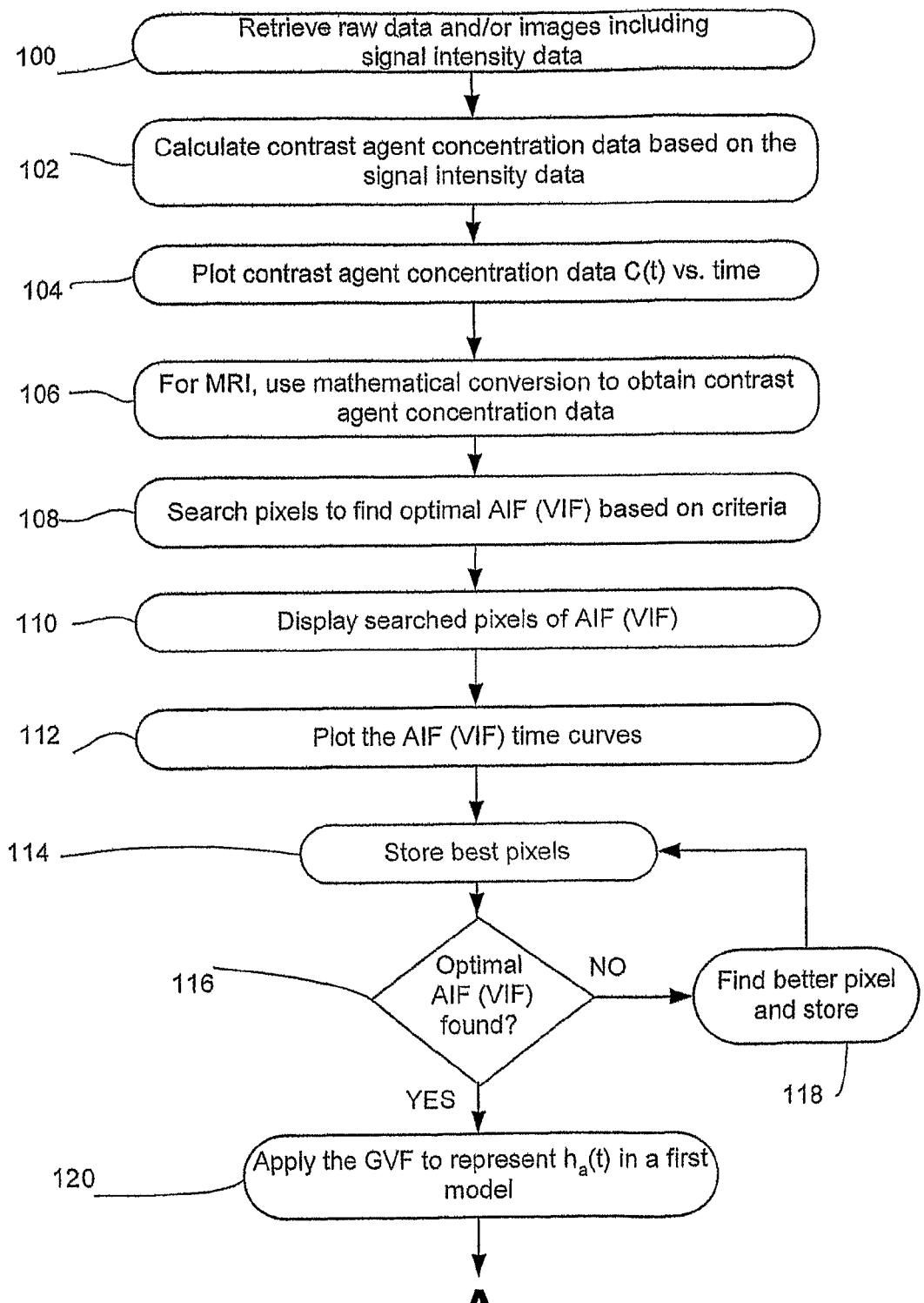
FIG. 5 is a flow diagram showing steps performed by a computer program to obtain values for the blood perfusion indices such as BF, BV and MTT.
Figure 5:
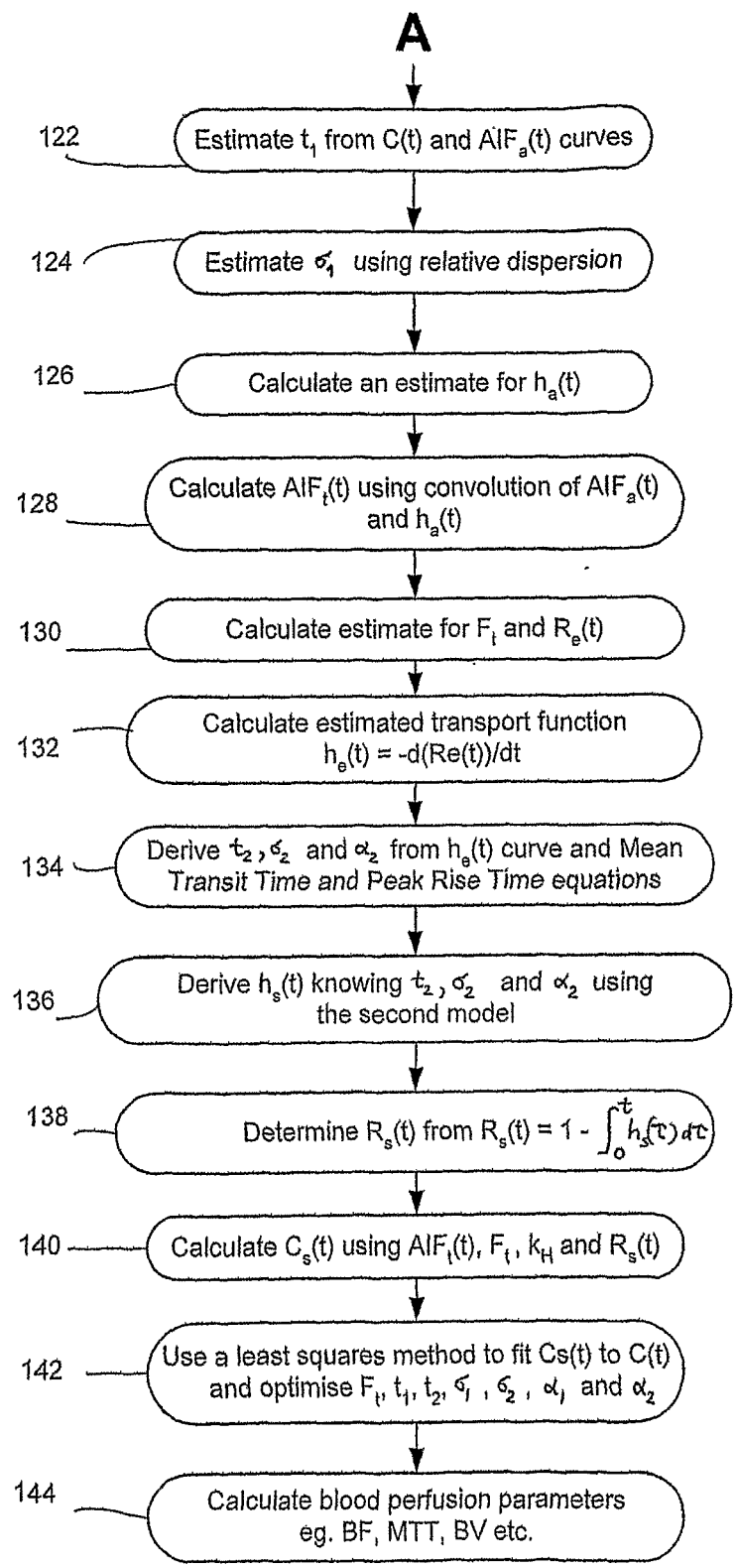

Referring to FIG. 5, the computer program at step 100 thus retrieves raw data and/or images from any one of the scanners 20, 30, 35 or PACS 40, including the signal intensities containing information of the contrast agent. At step 102 the program calculates the contrast agent concentration based on the signal intensities. It then plots the contrast agent concentration profile C(t) against time at step 104. Where the data is retrieved from an MRI scan, the signal intensities are converted mathematically to obtain C(t) at step 106. At step 108 the program searches pixels taken from the plots to find an optimal AIF (VIP) based on given criteria such as arrival times and peaks. At step 110 the program displays the searched pixels of the AIF (VIF) and plots these as a function of time at step 112. The best pixel(s) to date are then stored in memory means, such as located at computer 50, at step 114. A decision is made at step 116 to determine if the optimal pixel has been found and stored, which decision can be made by the user. If an optimal pixel has not been found, the program keeps reverting to step 118 to find a better pixel than the pixel stored, which is subsequently stored at step 114. When an optimal pixel has been found the process moves to step 120, to be described hereinafter.

The amount of contrast agent passing through the tissue 6 may then be measured by the computer program, the contrast agent concentration being represented as C(t).

Thus two known profiles are used by the computer program, one for the concentration of the contrast agent C(t) and the other for $AIF_a(t)$, being the arterial input function in the vessel (artery) leading to the ROI, against time. By knowing these two particular profiles the tissue blood flow $F_t$ and tissue impulse residue function (IRF), R(t), can be derived from a deconvolution of the equation $C(t)=(F_t/k_H) AIF_a(t) \otimes R(t)$, where $k_H=(1-H_a)/(1-H_t)$ is a correction constant taking into account different values of arterial hematocrit $H_a$ and tissue hematocrit $H_t$ since the contrast agent remains in the extracellular fraction of blood (plasma). The hematocrit is the volume fraction of cells in the blood, which has a typical value of $H_a \approx 0.45$ for large vessels such as the artery and a value of $H_t \approx 0.25$ for small vessels such capillaries in tissue.

In other words the concentration of the contrast agent is derived by a convolution of the arterial input function and the tissue IRF multiplied by the tissue blood flow. This is the case where there is no delay or dispersion so that the selected $AIF_a(t)$ from a major artery is taken to be the same as the $AIF_t(t)$ directly feeding the tissue.

Figure 3:
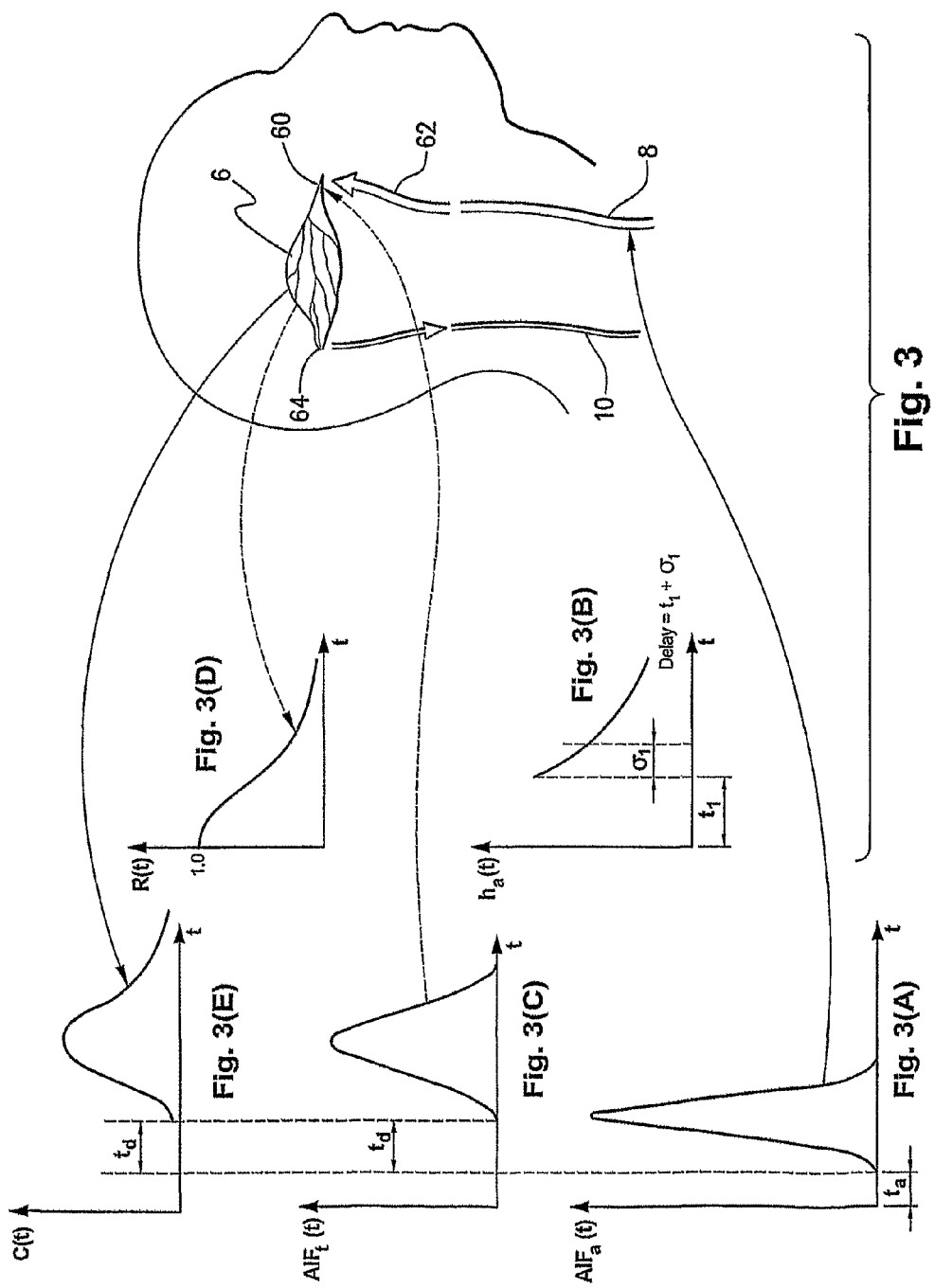
FIG. 3 shows various graphs against time at different parts of the subject's head as the contrast agent traverses the region of interest and the input artery.

In practice however it is difficult to measure the arterial input function at the input to different tissues of interest. This is due to the practicalities that, arteries directly feeding the tissues are usually small in size and subject to a substantial partial voluming effect. In the case of major vessel disease such as acute stroke or carotid artery stenosis, the AIF selected from a major artery is often associated with a delay and dispersion before it reaches the abnormal tissue of interest. As an example reference is made to FIG. 3 where the arterial input function is measured in artery 8 resulting in the graph of FIG. 3(A). It can be seen from the graph that there is a time $t_a$ taken from injection for the contrast agent to arrive at the point where the arterial input function is measured in artery 8. It results in a narrow 'pulse' having a large amplitude. Then in FIG. 3(C) there is shown the arterial input function if measured at the tissue 6 input artery designated by 60. It can be seen that the graph has dispersed somewhat or broadened, as well as involving a time delay $t_d$ in traversing the smaller artery 62 where a vessel disease such as stroke or stenosis may occur. Other normal small arteries supplying different tissues may have little delay and dispersion. Therefore it is practically useful to select a normal large vessel such as the internal carotid artery (ICA), middle cerebral artery (MCA), anterior cerebral artery (ACA) or posterior cerebral artery (PCA) through multiple slices in the head and neck of the patient. The transit of the contrast agent from the artery 8 through the artery or arteries 62 up to the entry point 60 of the tissue 6 is described by the vascular transport model (VTM) using the delay $t_d$ and an estimated dispersion parameter to derive a simulated function $AIF_t(t)$ at the tissue input artery 60. The next part of the transit of the concentration of the contrast agent is described by the tissue perfusion model (TPM) where the contrast agent traverses across the tissue 6 from an input 60 to an output 64. The measured contrast concentration profile C(t) represents the contrast agent remaining in the tissue 6 as represented by the curve shown in FIG. 3(E) and the tissue blood flow $F_t$ and impulse residue function (IRF) $R_e(t)$ can be estimated using a model-free deconvolution technique such as the singular value decomposition (SVD) method. However, such deconvolution is sensitive to noise, which may produce some mathematical solutions of $R_e(t)$ but without any physiological meaning. Further, the estimated $F_t$ and $R_e(t)$ may not be accurate due to uncertainties associated with unaccounted delay and dispersion effects. It is desirable to use a constrained deconvolution process using a model derived IRF $R_s(t)$ with a typical shape as shown in FIG. 3(D). The estimated $R_e(t)$ can be used to derive parameters for $R_s(t)$.

A simulated tissue contrast concentration curve derived using convolution as $C_s(t)=(F_t/k_H)AIF_t(t) \otimes R_s(t)$ can be fitted to the measured C(t) curve by optimizing the model parameters through an iterative least square method.

The gamma-variate function (GVF), represented by equation (1) below, has been generally used to describe the temporal profile of contrast during blood circulation through the vascular system.

$$GVF = \begin{cases} \frac{1}{A}(t-t_0)^\alpha e^{-(t-t_0)/\sigma} & (t \geq t_0) \\ 0 & (t < t_0) \end{cases} \quad (1)$$

In order to account for the delay and the dispersion through the artery 62 the computer program employs a first model of GVF to represent a vascular transport function as $$h_a(t) = \begin{cases} \frac{1}{A_1}(t-t_1)^{\alpha_1} e^{-(t-t_1)/\sigma_1} & (t \geq t_1) \\ 0 & (t < t_1) \end{cases} \quad (2)$$

Where $A_1 = \sigma_1^{1+\alpha_1}\Gamma(1+\alpha_1)$ since $\int_0^\infty h_a(t)dt \equiv 1$, $\Gamma(a) \equiv \int_0^\infty x^{\alpha-1}e^{-x}dx$ is the Gamma function, $t_1$ is the time taken for the initial $AIF_a(t)$ measured from artery 8 to arrive at artery 60 and $\sigma_1$ and $\alpha_1$ are related to the mean transit time and dispersion of $h_a(t)$. If setting $\alpha_1 = 0$, equation (2) becomes, $$h_a(t) = \begin{cases} \frac{1}{\sigma_1} e^{-(t-t_1)/\sigma_1} & (t \geq t_1) \\ 0 & (t < t_1) \end{cases} \quad (3)$$

An example plot of $h_a(t)$ versus time is shown in FIG. 3(B). The value of $t_1$ can be estimated by $t_d$ as the delay between C(t) in FIG. 3(B) and $AIF_a(t)$ in FIG. 3(A). Starting with an estimate of $\alpha_1 = 0$, the mean transit time of $h_a(t)$ is $t_1+\sigma_1$, and a relative arterial dispersion is defined as $\beta_1 = \sigma_1/(t_1+\sigma_1)$ ranging from 0 to 1. A relative dispersion value of $\beta_1 = 12\%$ is chosen based on previous measurements of dispersions typical for arteries (12%), vein (30%) and whole organs (40%). Thus an initial estimate of $\sigma_1$ can be obtained as $t_1\beta_1/(1-\beta_1)$.

Referring again to FIG. 5, at step 120 the computer program applies the GVF to represent $h_a(t)$ in a first model. At step 122 an estimate of $t_1$ is made from the plots of C(t) and $AIF_a(t)$. Then at step 124, the program estimates $\sigma_1$ using $t_1$ and a relative dispersion value $\beta_1$ assuming $\alpha_1 = 0$. The process then moves to step 126.

With the estimated $t_1$, $\alpha_1$ and $\sigma_1$ values, the estimated $h_a(t)$ function in equation (2) can be calculated by the computer program at step 126 to describe the arterial transport by $$AIF_t(t) = AIF_a(t) \otimes h_a(t) \quad (4)$$

where $AIF_t(t)$ is the arterial input function at the input to the tissue designated by 60, $AIF_a(t)$ is the initial AIF at artery 8 and $\otimes$ is the convolution operator.

The contrast concentration profile in the tissue of interest can be further determined by $$C(t) = (F_t/k_H)AIF_t(t) \otimes R_e(t) \quad (5)$$

where $k_H = (1-H_a)/(1-H_t)$ is a correction constant taking into account different values of arterial hematocrit $H_a$ and tissue hematocrit $H_t$ because the contrast agent remains in the extracellular fraction of blood (plasma). The hematocrit is the volume fraction of cells in the blood, which has a typical value of $H_a \approx 0.45$ for large vessels such as the artery and a value of $H_t \approx 0.25$ for small vessels such capillaries in tissue.

With measured C(t) and the model derived $AIF_t(t)$, an estimate of $F_t$ and $R_e(t)$ can be obtained using a model-free deconvolution technique such as the singular value decomposition (SVD) method. The deconvolution is very sensitive to noise, which may produce some mathematical solutions of $R_e$ but without any physiological meaning. Further, the estimated $F_t$ and $R_e(t)$ may not be accurate due to uncertainties associated with the initial estimate of $t_1$, $\alpha_1$ and $\sigma_1$ values. It is desirable to use a constrained deconvolution process using a model derived IRF with a typical shape as shown in FIG. 3(D).

Again referring to FIG. 5, the computer program stored in memory of the computer 50 directs the computer at step 128 to calculate an estimate for $AIF_t(t)$ from the convolution of $AIF_a(t)$ and $h_a(t)$ in equation (4) and at step 130 to calculate an estimate for $F_t$ and $R_e(t)$ from equation (5).

A more realistic (simulated) profile of the tissue IRF can be provided by the second model of GVF, which describes the tissue transport function as $$h_s(t) = \begin{cases} \frac{1}{A_2}(t-t_2)^{\alpha_2} e^{-(t-t_2)/\sigma_2} & (t \geq t_2) \\ 0 & (t < t_2) \end{cases} \quad (6)$$

Where $A_2 = \sigma_2^{1+\alpha_2}\Gamma(1+\alpha_2)$ $t_2$, $\sigma_2$ and $\alpha_2$ are parameters related to the mean transit time and dispersion of $h_s(t)$ through the tissue. If assuming $t_2 = 0$, equation (6) becomes $$h_s(t) = \frac{1}{A_2} t^{\alpha_2} e^{-t/\sigma_2} \quad (t \geq 0) \quad (7a)$$

Several typical characteristic parameters of $h_s(t)$ are determined as

Peak rise time (RT) = $\sigma_2 \alpha_2$

Mean transit time (MTT) = $\sigma_2(1+\alpha_2)$ \quad (7b)

Alternately, if assuming $\alpha_2 = 0$, equation (6) becomes $$h_s(t) = \begin{cases} \frac{1}{\sigma_2} e^{-(t-t_2)/\sigma_2} & (t \geq t_2) \\ 0 & (t < t_2) \end{cases} \quad (8a)$$

Several characteristic parameters of $h_s(t)$ are determined as

Peak height (PH) = $1/\sigma_2$

Mean transit time (MTT) = $t_2+\sigma_2$ \quad (8b)

The relationship between the tissue IRF R(t) and transport function h(t) is $$R(t) = 1 - \int_0^t h(\tau)d\tau \Rightarrow h(t) = -\frac{dR(t)}{dt} \quad (9)$$

Since h(t) is a probability density function, R(t) is a positive, decreasing function of time with a property of with R(0) = 1 as shown in FIG. 3(D).

From the estimated $R_e(t)$ profile deconvolved from equation (5), an estimated transport function $h_e(t)$ can be derived as $h_e(t) = -dR_e(t)/dt$. The peak rise time and mean transit time of $h_e(t)$ can then be calculated and used to estimate $\sigma_2$ and $\alpha_2$ using equation (7b) or to estimate $\sigma_2$ and $t_2$ using equation (8b) respectively.

Knowing the estimates of $\sigma_2$ and $\alpha_2$ with $t_2 = 0$, or knowing $\sigma_2$ and $t_2$ with $\alpha_2 = 0$, these are then input to equation (6) to determine a simulated transport function $h_s(t)$. The simulated tissue IRF $R_s(t)$ can then be determined from equation (9) as below:

$$R_s(t) = 1 - \int_0^t h_s(\tau)d\tau \qquad (10)$$

Once $R_s(t)$ is determined, then the simulated concentration curve can be determined as follows.

$$C_s(t) = (F_t/k_H)AIF_t(t) \otimes R_s(t) = (F_t/k_H)\int_0^t AIF_t(\tau)R_s(t-\tau)d\tau \qquad (11)$$

Using the computer program, the user selects the initial AIF and VIF, the program will automatically derive the $AIF_t(t)$ input to the tissue 6 based on the first model and the convolution thereof. Secondly the program will estimate tissue blood flow $F_t$ and IRF $R_e(t)$ and derive parameter values used to build the simulated tissue IRF $R_s(t)$ in the second model. The program further calculates a simulated contrast curve at the tissue of interest. The seven parameters $F_t$, $t_1$, $\sigma_1$, $\alpha_1$, $\sigma_2$, $\alpha_2$ and $t_2$ are optimized through a least squares method in order to fit the simulated $C_s(t)$ to the measured tissue curve $C(t)$. A toast squares fit can be represented by a minimization process of the quantity S defined in equation (12) below:

$$S = \sum_t (C(t) - C_s(t))^2 \qquad (12)$$

With the optimized seven parameters $F_t$, $t_1$, $\sigma_1$, $\alpha_1$, $\sigma_2$, $\alpha_2$ and $t_2$, several quantitative perfusion indices can be determined as Blood Flow (BF)=$F_t$ Mean Transit Time (MTT)=$t_2 + \sigma_2(1+\alpha_2)$ Blood Volume (BV)=BF*MTT Arterial Delay Time (DT)=$t_1 + \sigma_1(1+\alpha_1)$ Arterial Dispersion Time (ADT)=$\sigma_1\sqrt{1+\alpha_1}$ Tissue Dispersion Time (TDT)=$\sigma_2\sqrt{1+\alpha_2}$ Relative Arterial Dispersion (RAD)=ADT/DT Relative Tissue Dispersion (RTD)=TDT/MTT  (13)

These indices can be determined on a pixel-by-pixel basis to produce quantitative perfusion maps respectively for further analysis and interpretation.

This provides more accurate information to a clinician so that the clinician can decide on appropriate therapy for the patient on retrieving the above results or data.

Thus referring again to FIG. 5, at step 132 an estimate of the transport function across the ROI is calculated by the computer program using the equation $$h_e(t) = -\frac{d}{dt}R_e(t).$$

At step 134 the program derives $t_2$, $\sigma_2$ and $\alpha_2$ (with either $\alpha_2=0$ or $t_2=0$) from the $h_e(t)$ curve using the equations (7b) or (8b). At step 136 $h_s(t)$ is derived by the program knowing the values for $t_2$, $\sigma_2$ and $\alpha_2$ using the second model. At step 138 $R_s(t)$ is derived from equation (10) by the program. At step 140 $C_s(t)$ is determined by the program using the estimates for $R_s(t)$, $AIF_t(t)$, $k_H$ and $F_t$. At step 142 a least squares method is used by the program to fit $C_s(t)$ to $C(t)$ and to optimize the parameters $F_t$, $t_1$, $\sigma_1$, $\alpha_1$, $\sigma_2$, $\alpha_2$ and $t_2$ by minimising S in equation (12) iteratively. Finally at step 144 the program calculates values for perfusion indices such as BF, MTT and BV etc using equation (13).

An artery is usually selected in the process of obtaining an arterial input function, however in the brain it is not always easy to obtain a major artery. A smaller artery in the brain may be selected instead leading to partial voluming. To compensate for partial voluming, a vein that is much larger than the artery and is usually easy to identify may be used. The user and/or computer program searches for a large vein which should have minimal partial voluming effect. A smaller artery can be selected and scaled against a vein profile. Thus, a profile of a VIF from a large draining vein is determined. The AIF is then scaled up to have the same first-pass bolus peak area as the VIF to minimise the PV effect from the AIF. The first-pass AIF and VIF profiles can be obtained by fitting them to the GVF profiles respectively to remove contrast recirculation effects. The area under the vein profile should be the same as the arterial profile. However, this approach of using a $VIF_a(t)$ to correct for partial volume effects of $AIF_a(t)$ is not applicable outside the brain as the contrast agent does not always remain within the vascular system during transit through the body. Usually in the body a large artery without partial voluming can be found on the imaging slices.

Figure 4:
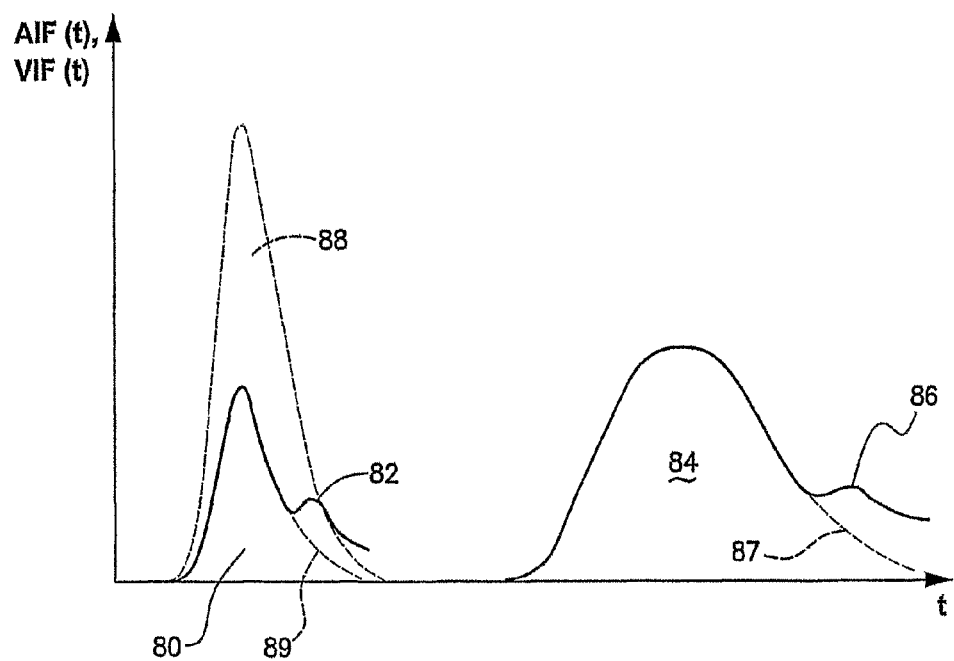
FIG. 4 shows a plot whereby an input arterial profile for a small artery exhibiting partial voluming is scaled up based on a vein profile.

Thus in FIG. 4 the AIF profile 80 of the original artery selected is shown, which is much smaller than the expected profile due to partial voluming. Therefore a vein is selected and it has the VIF profile 84. Due to recirculation effects, each profile shows a local maximum 82 (on the AIF curve) and 86 (on the VIF curve). A GVF is fitted by the computer program to the VIF to obtain an estimate of the total area (BV) under the fitted VIP curve whilst eliminating the local maximum 86 and following contour 87. Then the GVF is applied by the computer program to the selected AIF to eliminate the local maximum 82 and extend the profile along contour 89. The program then uses this estimate to scale up the original AIF 80 to AIF 88 to obtain an estimate of the concentration of contrast agent from the scaled up AIF 88. This approach overcomes the problem when the VIF is represented partly with a missing end portion in the data due to a shorter scanning time in order to keep to a minimum the amount of time a patient has to spent being scanned by a particular scanner.

It is to be noted that the use of a GVF in each of the first and second models is for relative ease of calculations. Should the full GVF be used in both the first and second models, there will be seven adjustable parameters that need to be optimized by the least square fitting process. The computer program may provide various options to allow the user to fix certain parameters such as $\alpha_1=0$ and $t_2=0$ (or $\alpha_1=0$ and $\alpha_2=0$) throughout the least square fitting process, in which only five parameters $F_t$, $\sigma_2$, $\alpha_2$, $\sigma_1$ and $t_1$ (or $F_t$, $\sigma_2$, $t_2$, $\sigma_1$ and $t_1$) would then need to be optimized. The computer program further allows the user to fix the relative arterial dispersion $\beta_1$ thus $\sigma_1$ can be calculated dependent on $t_1$. A fixed value of $\beta_1=12\%$ can be chosen based on previously published results.

Alternately, if one can measure $AIF_t(t)$ by identifying a small artery showing a delay relative to $AIF_a(t)$, optimized $\sigma_1$ and $t_1$ values can be determined by fitting the simulated $AIF_t(t)$ from equations (3) and (4) to the measured $AIF_t(t)$. Then a relative dispersion $\beta_1$ value can be determined and applied to all other pixels of the same subjects assuming a constant relative dispersion. Thus there will be only four parameters $F_t$, $\sigma_2$, $\alpha_2$ and $t_1$ (or $F_t$, $\sigma_2$, $t_2$ and $t_1$) that need to be optimized for increased robustness of the fitting process.

Furthermore, one may apply the above approach to various subjects with vascular abnormalities accompanied by delay and dispersion, such as in acute stroke and stenosis. Once a consistent relative dispersion value $\beta_1$ is determined from all the representing cases, the vascular transport function in equation (3) can be described by a single variable $t_1$ together with a constant $\beta_1$. A two-step method can be implemented to account for delay and dispersion. At first, an initial IRF $R_0(t)$ can be derived by deconvolution of $AIF_a(t)$ from $C(t)$ using the model-free SVD method. The delay time $t_1$ can be determined by the maximum position of $R_0(t)$, i.e. $R_{0max} \equiv R_0 (t=t_1)$. The $t_1$ value determined this way is less sensitive to curve noise because the deconvolution involves all data points of the time curve. In the second step, the $AIF_t(t)$ feeding the ROI can be derived from equation (3) with $t_1$ and the constant $\beta_1$, which determine $\sigma_1$. Then value of $F_t$ and corrected IRF $R_e(t)$ can be obtained by deconvolution of the model derived $AIF_t(t)$ from $C(t)$ using the SVD method. Perfusion indices can be determined from the calculated $R_e(t)$ curve as $MTT=\int_0^\infty R_e(\tau)d\tau$, $BF=F_t$ and $BV=BF*MTT$. This approach can be implemented via a computer program for fast processing of perfusion maps by accounting for delay and dispersion without a time-consuming least-square-fitting process.

Alternatively, as the transport function $h(t)$ is simply a probability distribution function of the transit times, it is possible to use other functions such as a modified Gaussian function in equation (14) below to substitute equation (1) hence to describe $h_a(t)$ and $h_s(t)$ respectively.

$$h(t) = \begin{cases} \frac{1}{A}e^{-(t-t_0)^2/2\sigma^2} & (t \geq 0) \\ 0 & (t < 0) \end{cases} \quad (14)$$

Where $t_0 \geq 0$, $A=\sqrt{2\pi}\sigma[1+\text{erf}(t_0/\sqrt{2}\sigma)]/2$ and $$\text{erf}(t) \equiv \frac{2}{\sqrt{\pi}} \int_0^t e^{-x^2} dx$$

is the error function. Using the Gaussian function to substitute the first and second models in equations (3) and (8a) respectively, there are five parameters ($F_t$, $\sigma_2$, $t_2$, $\sigma_1$ and $t_1$) that need to be optimized through the fitting process.

Furthermore, the two models are not limited in scope to use in major vessel disease associated with the head of a patient, such as acute stroke or carotid artery stenosis. The models can be used in any intra-vascular application and therefore can apply to different parts of a patients body, such as the cortex of the kidneys, lungs or spleen.

The models can be further extended to other cases where contrast may not totally remain intravascular but leak into the tissue, such as in a tumour. For a tissue ROI with a mean transit time of $\tau$, the tissue IRF can be described by the adiabatic approximation to the tissue homogeneity model as $$R(t, \tau) = \begin{cases} 1 & (t \leq \tau) \\ Ee^{-k(t-\tau)} & (t > \tau) \end{cases} \quad (15)$$

where the first term is the intravascular component and the second term is the leakage component. E is the extraction fraction of the tracer in the blood stream that leaks out of the vessel into tissue, and the tracer clearance rate constant $k=E*F_t/V_e$ is a rate constant at which the leaked contrast agent diffuses back into the blood stream and leaves the tissue, $V_e$ is the volume fraction of the extravascular and extracellular space (EES) in the tissue.

Normally there is perfusion heterogeneity associated with a distribution of transit time $\tau$ of blood vessels in tissue. Such a distribution can be described by a probability density function $h_s(\tau)$ such that the average tissue IRE involving leakage becomes $$R_s(t)=1-\int_0^t h_s(\tau)d\tau+Ee^{-kt}\int_0^t h_s(\tau)e^{k\tau}d\tau \quad (16)$$

where $h_s(\tau)$ can be described by the GVF model of equation (1) or by a Gaussian distribution function of equation (14).

The above described method for intravascular perfusion can be extended for perfusion measurements in a tumour by substituting equation (10) with (16) for the simulated $C_s(t)$ in equation (11). With two additional parameters, E and $V_e$ (or k), the method described above can be used to derive parameters for measuring both blood perfusion and permeability related indices including $F_t$, E and $V_e$. The parameters E and $V_e$ have a value between zero and one. The program selects certain starting values of E and $V_e$ such as E=0.2 and $V_e$=0.4, then further optimizes E and $V_e$ together with all other adjustable parameters (e.g $F_t$, $\sigma_2$, $\alpha_1$, $\sigma_1$, $t_1$, $\alpha_2$, and $t_2$) using the least squares method of equation (12). The permeability surface area product can then be determined by $PS=-F_t \ln(1-E)$, where $PS=E*F_t$ when $E<<1$.

Figure 6:
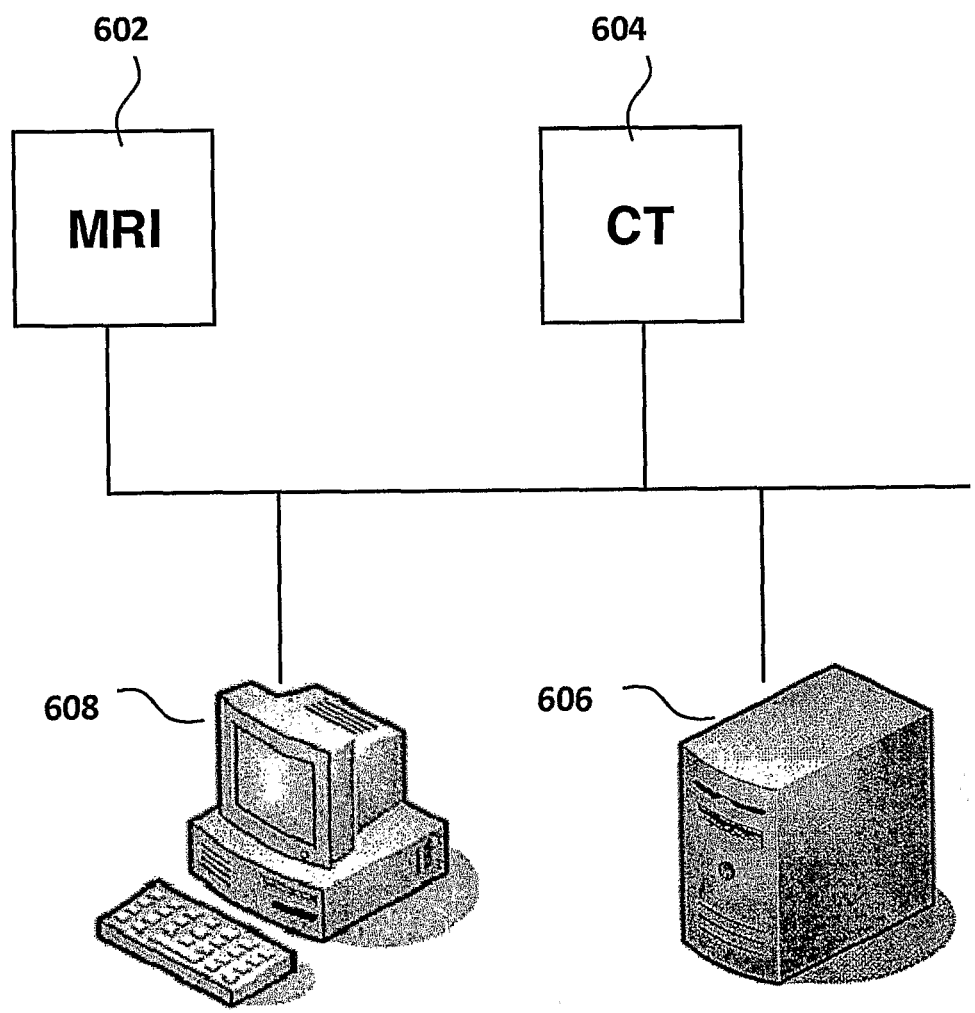
FIG. 6 is a block diagram showing a communication network including a number of scanners linked to a data storage system and a processing system.

The present invention is particularly applicable to CT and MRI dynamic perfusion imaging which involves intravenous injection of a contrast bolus into a patient. Raw data and/or images acquired by a scan, such as from a CT scanner 602, MRI scanner 604 are forwarded to a data storage system 606 in the form of a Picture Archiving Communications System (PACS) in FIG. 6. A computer program operating on a processor 608, in the form of a computer, is used to retrieve the various images or raw data from any one of the scanners 602, 604 or from the data storage system 606. The computer program need not reside on computer 608, but may reside in a console computer linked to any one of the scanners 602 or 604. Alternatively the program may reside in a workstation (stand-alone or in a system) or in the PACS 608.

Figure 7:
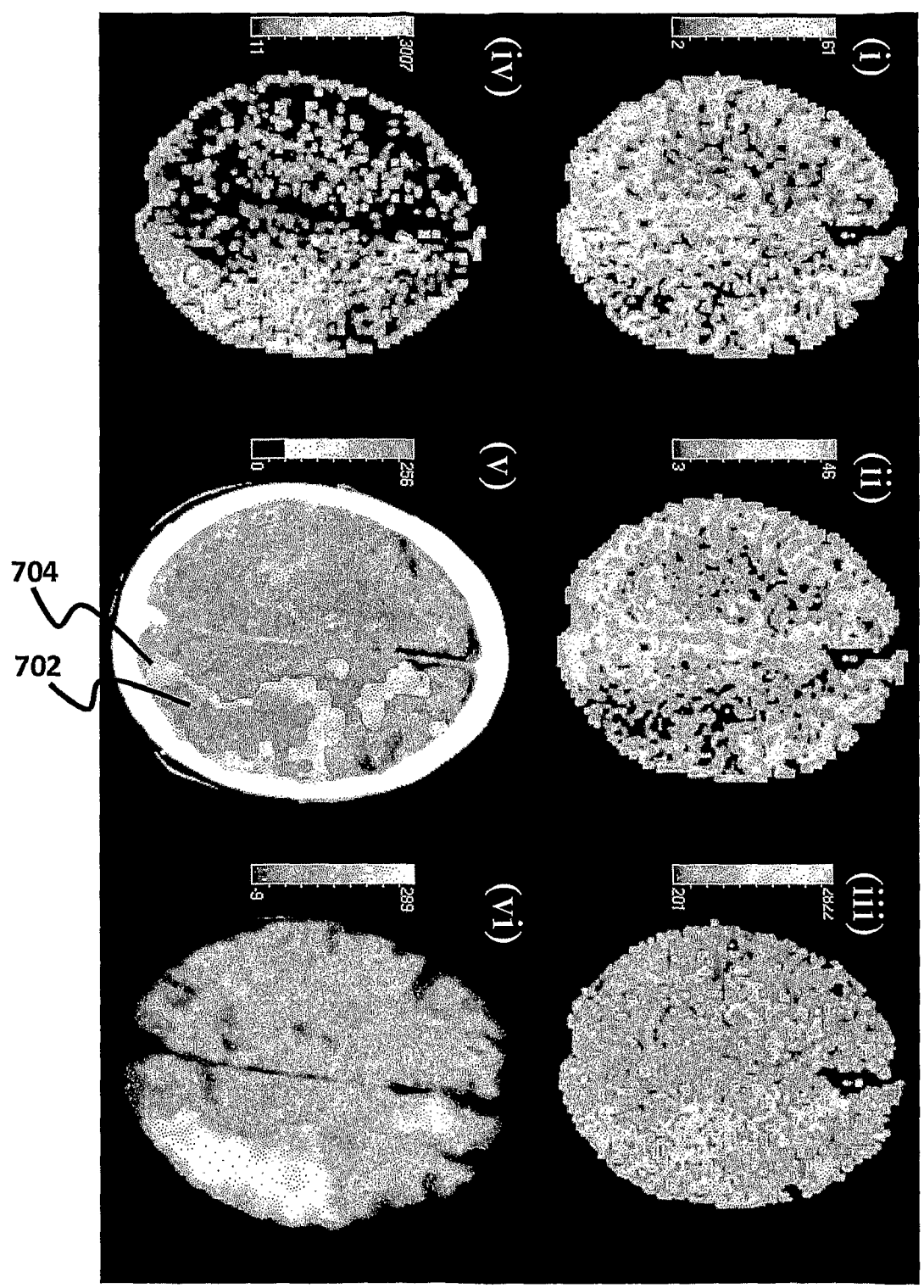
FIG. 7 (i)-(v) shows the perfusion and tissue status maps of an acute stroke patient: (i) CBV, (ii) CBF, (iii) MTT, (iv) DT, and (v) tissue status map including the infarct (red) 702 surrounded by the penumbra (green) 704. The acute penumbra progressed to subacute infarct as shown in FIG. 2(vi) by the bright intensity region on the diffusion-weighted MRI scanned one day later.
Figure 8:
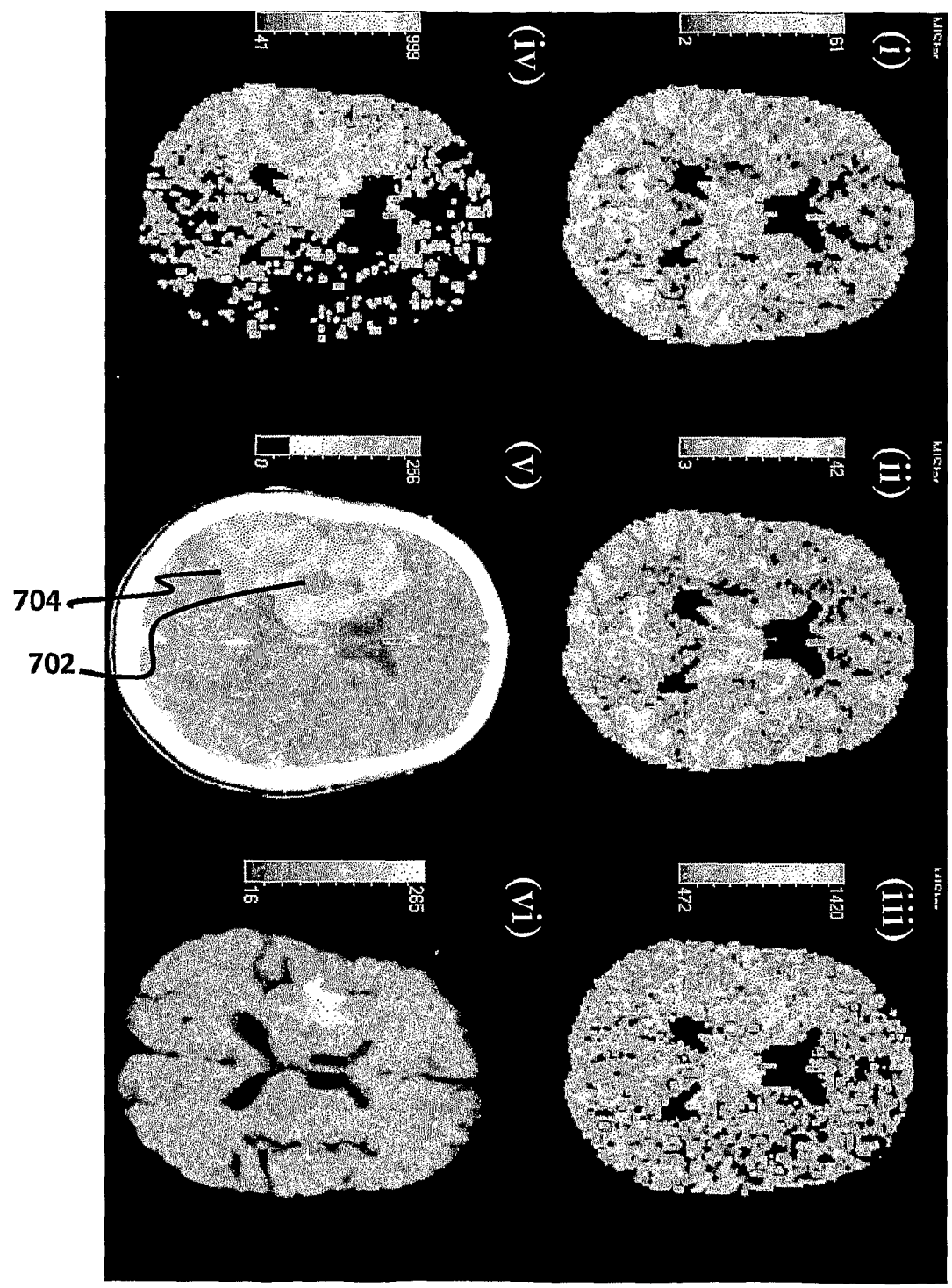
FIG. 8 (i)-(v) shows the perfusion and tissue status maps of an acute stroke patient: (i) CBV, (ii) CBF, (iii) MTT, (iv) DT, and (v) tissue status map including the infarct (red) 702 surrounded by the penumbra (green) 704. The majority of the acute penumbra did not progress to further infarct by subacute stage as shown in FIG. 3(vi) by the diffusion-weighted MRI scanned one day later.

The program loads the dynamic perfusion data and/or images, then process them to produce various perfusion maps including CBV, VBF, MTT and DT, and further create a color-coded tissue status map consisting of an infarct (red) 702 and penumbra (green) regions overlaid on the corresponding raw image. FIG. 7 shows an example of acute ischemic penumbra detected by the current method in an acute stroke patient, however without effective treatment, the initial penumbra region further progressed to infarction by the next day. In contrast, with early intervention, the penumbra region detected by the current method in another acute stroke patient was mostly salvaged (with only little expansion of the infarct core) by the next day, as shown in FIG. 8. These two examples demonstrate that the ischemic penumbra and infarct identified by the current method has the potential to more accurately reflect the tissue status at the acute stage, hence the tissue status map together with penumbra measure as percentage of the total ischemic lesion can be expected to produce better outcome when used to guide treatment of acute stroke patient.

Figure 9:
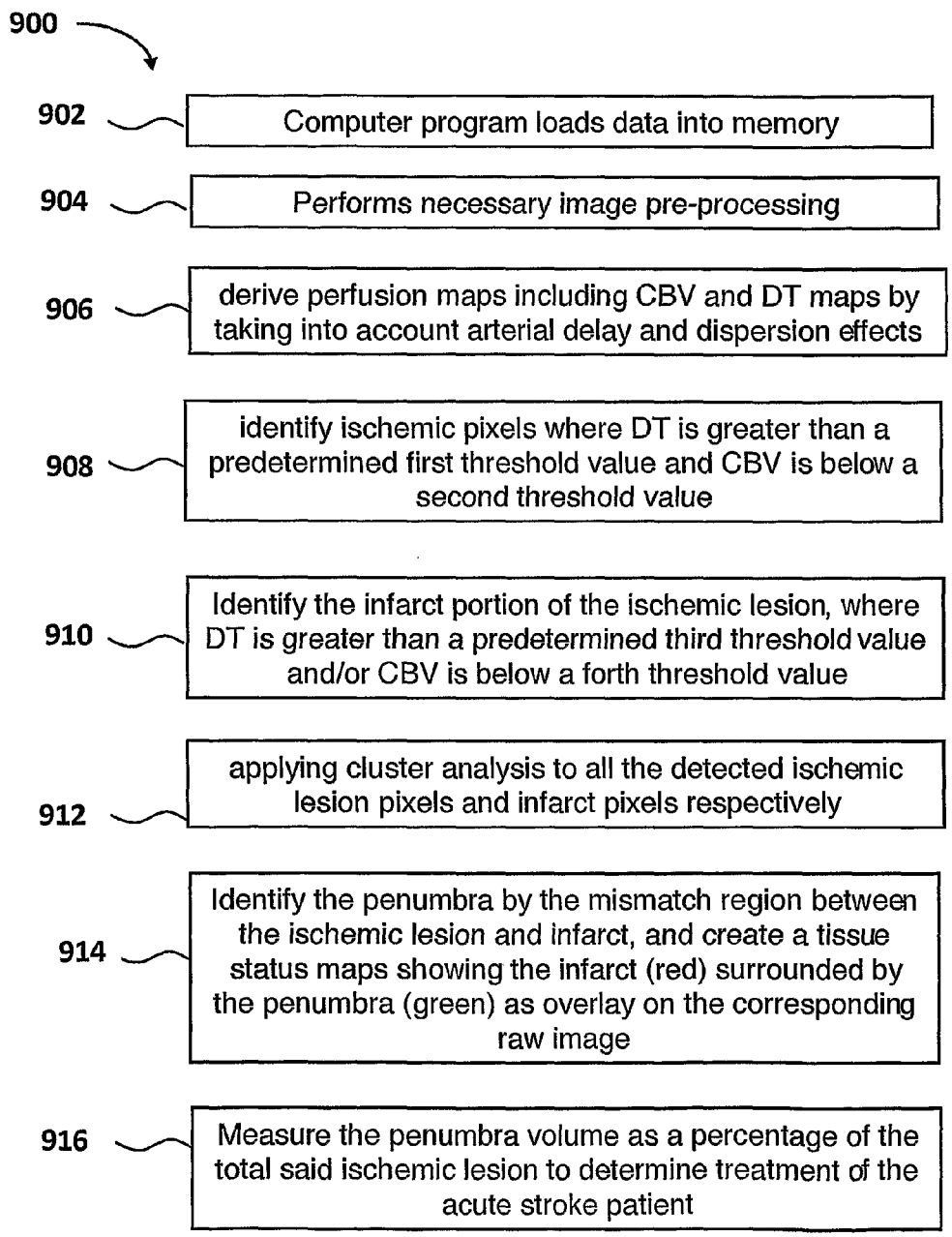
FIG. 9 is a flow diagram showing steps performed by a computer program to process various perfusion maps, then to create the tissue status map showing the ischemic penumbra and infarct to guide treatment of the acute stroke patient.

With reference to FIG. 9 there is shown a flow diagram 900 of the steps taken by a computer program to load data and/or images into memory at step 902, where the data has been retrieved from any one of the scanners 602, 604 or PACS 606, including the signal intensities containing information of the contrast agent. At step 904 the program performs various pre-processing including (i) motion correction; (ii) detection of AIF and VOF; (iii) setting baseline time period before contrast arrival; and (iv) converting a signal intensity profile to contrast concentration time curve.

At step 906, the program process data on a pixel-by-pixel basis to produce various perfusion maps using a model-free deconvolution technique such as the singular value decomposition (SVD) technique by taking into account arterial delay and dispersion effects. Deconvolution of the AIF from the tissue time curve produces the tissue IRF, where the maximum of the IRF appears at certain time point, Tmax. To properly taking into account arterial delay and dispersion effects, an iterative deconvolution approach is applied by looping through a series of delay time values, $DT_i$, ranging from 0 to Tmax. For each delay time, a modelled arterial transport function is convolved with the measured global $AIF_g$ to produce an $AIF_i$, which is used for SVD deconvolution of the tissue curve to generate an IRF; with its maximum appears at Tmax(i). The actual delay time, DT, is determined as the minimum $DT_i$ value which produces Tmax(i)=0. Subsequently, CBF and CBV can be determined by the maximum and integral of $IFR_i$ respectively, with MTT=CBV/CBF.

At step 908, the program identifies ischemic pixels where DT is greater than a predetermined first threshold value and CBV is below a second threshold value.

At step 910, the program identifies the infarct portion of the ischemic lesion, where DT is greater than a predetermined third threshold value and/or CBV is below a forth threshold value.

At step 912, the program may further apply cluster analysis to all the detected ischemic pixels and infarct pixels respectively by removing small islands or filling small holes with maximum cluster size below a predetermined fifth threshold value. The cluster analysis may involve general morphological operators such as opening and closing, or the general k-means clustering technique.

The ischemic penumbra can be identified at step 914, by the mismatch region between the ischemic lesion and infarct. Then a tissue status map can be created to display the infarct (red) 702 surrounded by the penumbra (green) 704 as a color overlay on the corresponding raw image.

At step 916, the program measures the penumbra volume as a percentage of the total said ischemic lesion to determine treatment of the acute stroke patient.

This embodiment has been described using an example of CT perfusion imaging in acute stroke patients. The invention is equally applicable to animals as well, and using MRI scans.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed is:

1. A method of identifying ischemic lesions in a subject, by operating a computer program on perfusion imaging data input to a computer comprising:
   a. loading said perfusion imaging data into an electronic memory means, wherein said perfusion imaging data contains information of a contrast agent passing through a region of interest (ROI), wherein said ROI comprises tissue;
   b. measuring a global arterial input function AIF from a normal major artery, wherein said AIF is an intensity profile measured against time;
   c. measuring a tissue contrast agent curve C(t) in said tissue, wherein said C(t) is an intensity profile measured against time;
   d. deriving perfusion maps by deconvolution of said AIF from said C(t) on a pixel-by-pixel basis using a delay and dispersion compensated deconvolution method, wherein said perfusion maps comprise an arterial delay time (DT) map and cerebral blood volume (CBV), cerebral blood flow (CBF) and mean transit time (MTT) maps;
   e. determining ischemic lesion pixels from said perfusion imaging data, wherein said DT is greater than a predetermined first threshold value and said CBV is below a second threshold value.
   f. applying a cluster analysis to said ischemic lesion pixels by removing small islands or filling small holes, wherein the said small island[s] or small holes have a maximum cluster size below a predetermined fifth threshold value.

2. The method according to claim 1 further comprising the step of determining the infarct portion of said ischemic lesion, wherein (i) said DT is greater than a predetermined third threshold value, or (ii) said CBV is below a forth threshold value, or (i) and (ii).

3. The method according to claim 2 may further comprise the step of applying a cluster analysis to said infarct pixels by removing small islands or filling small holes, wherein the said small island or small holes have a maximum cluster size below the predetermined fifth threshold value.

4. The method according to claim 2 further comprising the step of determining a penumbra by the mismatch regions between said ischemic lesion and said infarct.

5. The method according to claim 4 further comprising the step of determining a penumbra volume as a percentage of the said ischemic lesion volume.

6. The method according to claim 1, wherein:
   a. said predetermined first threshold value is approximately 3 to 4 seconds;
   b. said predetermined second threshold value is approximately 9 ml/100 g.

7. The method according to claim 2, wherein:
   a. said predetermined third threshold value is approximately 10 seconds;
   b. said predetermined forth threshold value is approximately 1.5 ml/100 g;
   c. alternatively, said predetermined forth threshold value is approximately 50% of the average CBV value measured from unaffected normal tissue of said subject.

8. The method according to claim 1, wherein said predetermined fifth threshold value is approximately 3 to 5 mm.

9. The method according to claim 1, in which step d) is performed by:
   a. calculating a tissue impulse residue function (IRF) by deconvolution of said AIF from said C(t) using a model-free deconvolution method, wherein the maximum of the IRF appears at certain time point, Tmax;
   b. looping through a series of delay time values, DTi, ranging from 0 to Tmax, wherein for each delay time value, an arterial transport function with a delay time DTi and a known relative dispersion factor is convolved with said AIF to produce an AIFi, wherein an IRFi is calculated by deconvolution of said AIFi from said C(t)

using said model-free deconvolution method, wherein the maximum of the IRFi appears at Tmax(i);

c. determining DT by the minimum DTi value which produces Tmax(i)=0; wherein the corresponding IRFi is recorded as IRFo;

d. determining CBF and CBV by the maximum and integral of said IRFo respectively, wherein MTT=CBV/CBF.

10. The method according to claim 1, in which step d) may be performed alternatively by:

a. simulating a tissue input function $AIF_t$ by convolving said AIF with a first model for a vascular transport function taking into account delay and dispersion effects;

b. simulating a tissue curve $C_s(t)$ by convolving said AIF with a second model for a tissue transport function;

c. using a least squares method to fit the said simulated $C_s(t)$ to said measured tissue curve C(t) by optimizing the values of at least four adjustable parameters;

d. using a model-free deconvolution method to estimate initial values of said adjustable parameters for said least squares fitting process in order to derive optimized values of said adjustable parameters; and e. calculating perfusion maps from said optimized values of adjustable parameters.

11. The method of claim 1, wherein said AIF is scaled upward according to a venous output function (VOF), wherein said VOF is based on a measured contrast intensity profile in a vein draining from said ROI.

12. A system of identifying ischemic lesions in a subject, the system comprising:

scanning means for acquiring a perfusion image data of the subject, wherein a contrast agent is administered to the subject during a dynamic imaging scan;

storage means for retrieving or receiving image data from the scanning means;

processor means comprising:

a. loading said perfusion imaging data into an electronic memory means, wherein said perfusion imaging data contains information of a contrast agent passing through a region of interest (ROI), wherein said ROI comprises tissue;

b. measuring a global arterial input function AIF from a normal major artery, wherein said AIF is an intensity profile measured against time;

c. measuring a tissue contrast agent curve C(t) in said tissue, wherein said C(t) is an intensity profile measured against time;

d. deriving perfusion maps by deconvolution of said AIF from said C(t) on a pixel-by-pixel basis using a delay and dispersion compensated deconvolution method, wherein said perfusion maps comprise an arterial delay time (DT) map and cerebral blood volume (CBV), cerebral blood flow (CBF) and mean transit time (MTT) maps;

e. determining ischemic lesion pixels from said perfusion imaging data, wherein said DT is greater than a predetermined first threshold value and said CBV is below a second threshold value.

f. applying a cluster analysis to said ischemic lesion by removing small islands or filling small holes, wherein the said small island[s] or small holes have a maximum cluster size below a predetermined fifth threshold value.

13. The system according to claim 12 further comprising the step of determining the infarct portion of said ischemic lesion, wherein (i) said DT is greater than a predetermined third threshold value, or (ii) said CBV is below a forth threshold value, or (i) and (ii).

14. The system according to claim 13 may further comprise the step of applying a cluster analysis to said infarct pixels by removing small islands or filling small holes, wherein the said small island or small holes have a maximum cluster size below a predetermined fifth threshold value.

15. The system according to claim 13 further comprising the step of determining a penumbra by the mismatch regions between said ischemic lesion and said infarct.

16. The system according to claim 15 further comprising the step of determining a penumbra volume as a percentage of the said ischemic lesion volume to guide treatment of the acute stroke patient.

17. The system according to claim 12, in which the scanning means is at least one of a computed tomography (CT) imaging system and a magnetic resonance imaging (MRI) system. The storage means is a data storage system such as a Picture Archiving Communications System (PACS).

* * * * *